US008138308B2

(12) United States Patent
Berry et al.

(10) Patent No.: US 8,138,308 B2
(45) Date of Patent: Mar. 20, 2012

(54) MODIFIED PEPTIDE SUBSTRATE

(75) Inventors: Leslie R. Berry, Burlington (CA); Vera Ignjatovic, Armadale (AU); Paul T. Monagle, East Bentleigh (AU); Anthony K. Chan, Ancaster (CA)

(73) Assignees: McMaster University, Hamilton, Ontario (CA); The University of Melbourne, Victoria (AU)

( * ) Notice: Subject to any disclaimer, the term of this patent is extended or adjusted under 35 U.S.C. 154(b) by 622 days.

(21) Appl. No.: 12/159,456

(22) PCT Filed: Dec. 21, 2006

(86) PCT No.: PCT/CA2006/002100
§ 371 (c)(1),
(2), (4) Date: Jun. 27, 2008

(87) PCT Pub. No.: WO2007/073597
PCT Pub. Date: Jul. 5, 2007

(65) Prior Publication Data
US 2009/0148845 A1    Jun. 11, 2009

Related U.S. Application Data

(60) Provisional application No. 60/753,410, filed on Dec. 27, 2005.

(51) Int. Cl.
*C07K 1/00* (2006.01)
(52) U.S. Cl. ............. 530/350; 530/300; 435/6; 435/7.1
(58) Field of Classification Search ........................ None
See application file for complete search history.

(56) References Cited

U.S. PATENT DOCUMENTS

| 5,192,689 | A | 3/1993 | Hemker |
| 5,591,591 | A | 1/1997 | Bronstein |
| 5,654,152 | A | 8/1997 | Koyama et al. |
| 6,403,092 | B1 | 6/2002 | Pizzo |
| 6,740,496 | B1* | 5/2004 | Hemker et al. ................. 435/13 |
| 7,550,282 | B2* | 6/2009 | Margel et al. ................. 435/219 |
| 2005/0209137 | A1 | 9/2005 | Gertler |
| 2005/0221414 | A1 | 10/2005 | Varadi |

FOREIGN PATENT DOCUMENTS

| WO | 2004/016807 | 2/2004 |
| WO | 2005/095638 | 10/2005 |

OTHER PUBLICATIONS

Halling, et al, "Understanding Enzyme Action on Immobilised Substrates", Biotechnology 2005, 16:385-392.
Horton, et al, "Macromolecular Chromogenic Substrates for Measuring proteinase Activity", Clinical Chemistry 47:2, 212-222 (2001).
Peetz, et al, "Analytical Evaluation of a Fully Automated Chromogenic Assay for the Determination of Endogenous Thrombin Potential (ETP)", Journal of Thrombosis and Haemostasis, vol. 3, Supplement 1, Aug. 2005, Abstracts from XXth 1STH Congress, Aug. 6-12, 2005.
Sottrup-Jensen, Lara, "α-*Macroglobulins: Structure, Shape, and Mechanism of Proteinase Complex Formation*", The Journal of Biological Chemistry, vol. 264, No. 20, Issue of Jul. 15, pp. 11539-11542, 1989.
Byun et al. "Binding kinetics of thrombin and antithrombin III with immobilized heparin using a spacer" ASAIO J. Jul.-Sep. 1992;38(3):M649-53.
Eriquez et al. "Purification by affinity chromatography and properties of a beta-lactamase isolated from *Neisseria gonorrhoeae*" Antimicrob Agents Chemother. Feb. 1979;15(2):229-234.
Sasaki et al. "Improved method for the immobilization of heparin", J Chromatogr. Jul. 29, 1987;400:123-132.
Tung et al. "A novel near-infrared fluorescence sensor for detection of thrombin activation in blood" Chembiochem. Mar. 1, 2002;3(2-3):207-211.

* cited by examiner

*Primary Examiner* — Hope Robinson
(74) *Attorney, Agent, or Firm* — Occhiuti Rohlicek & Tsao LLP

(57) ABSTRACT

The invention provides novel reagents and methodologies for detecting free versus bound compounds. It is particularly useful to detect thrombin when it is not bound to A2M in the presence of thrombin bound to A2M by using a modified substrate that is sterically hindered from reacting with the bound thrombin.

2 Claims, 5 Drawing Sheets

Well coated with chemiluminescent thrombin substrate

Plasma or blood added to well

Thrombin from activated plasma/blood reacts with substrate to give light

MODIFIED PEPTIDE SUBSTRATE

CROSS-REFERENCE TO RELATED APPLICATIONS

This application is the National Stage of International Application No. PCT/CA2006/002100, filed on Dec. 21, 2006, which claims the priority of U.S. Patent Application No. 60/753,410, filed on Dec. 27, 2005. The contents of both applications are hereby incorporated by reference in their entirety.

FIELD OF INVENTION

The present invention is directed to a modified substrate and assays and methods using the modified substrate to determine free versus bound protein entities.

BACKGROUND OF THE INVENTION

Alpha-2-macroglobulin (A2M) and related proteins share the function of acting as a molecular trap. Various types of compounds, such as hormones, growth factors, cytokines and proteins, can be "trapped" by A2M. A2M can bind both host and foreign peptides and particles. A2M is sometimes referred to as a panproteinase inhibitor since it can interact with a wide variety of proteinases. When captured by A2M, a proteinase is protected from large proteinase inhibitors and large substrates, but it can still interact with small inhibitors and substrates.

One A2M-proteinase association that has been well studied is the trapping of thrombin in A2M.

Thrombin is a pivotal enzyme in the coagulation cascade (2, 3) since it can, among other things, activate fibrinogen to form fibrin (4, 5), feedback to activate factors XI, VIII and V higher up in the coagulation cascade and activate platelets (2). Control of thrombin occurs, in part, via inhibition from the plasma proteins antithrombin (AT), heparin cofactor II and A2M. Reaction with AT is often the major inhibitory mechanism for control of thrombin activity in adults. However, in newborns and children, reaction with A2M is considered significant due to the elevated plasma concentrations of A2M compared to those of adults (6, 7, 8). Thrombin activation is hindered by A2M via cleavage of the A2M polypeptide chain, resulting in a conformational change in the 3-dimensional A2M structure to form a product in which the thrombin is captured within the A2M molecule (9, 10, 11). Within this thrombin-A2M complex, thrombin may also become covalently linked to the A2M through further reaction of thrombin amino groups with a thiol-lactone group on A2M (9,12).

Given the importance of thrombin in the coagulation system, it is becoming increasingly desirable to develop a system to measure the thrombin generating potential in plasma or blood from patients to assess their haemostatic status. Previous methodology for measuring thrombin generation has either involved subsampling of activated plasma to detect thrombin activity (13, 14, 15) or detection of thrombin continuously using substrate mixed into the thrombin generating activated plasma (16, 17, 18). A major drawback of previous procedures for determining thrombin generation is that the reagents used to detect thrombin activity detect thrombin bound to A2M as well as thrombin not bound to A2M. In the case of subsampling methods, activity in assays of thrombin-A2M reaction with substrate (detected after neutralization of free unbound thrombin with added AT+heparin) are subtracted from assays for total thrombin activity to obtain free physiologically active thrombin concentrations. However, these experiments are laborious and require two thrombin generation assays to be carried out on each plasma sample. In addition, subsampling analyses cannot be done on coagulating plasma or blood. Alternatively, continuous measurement of thrombin generation using thrombin substrates added to the activated thrombin generating system (plasma, blood, etc) are unable to directly measure generation of thrombin that is not bound to A2M. In the continuous assays, theoretical amounts of physiologically active thrombin are determined by subtracting a calculated hypothetical curve of thrombin-A2M generation from the measured thrombin+thrombin-A2M data.

Various attempts have been made to develop assays that can measure the thrombin potential in plasma and blood. For example, U.S. Pat. No. 5,192,689 to Hemker et al. is directed to a method for determining the endogenous thrombin potential of plasma and blood. However, the patented method measures total thrombin activity, which includes thrombin alone as well as thrombin bound to A2M. The thrombin activity is measured using small chromogenic/fluorogenic substrates, followed by a calculated estimate of thrombin bound to A2M which is then subtracted from the total thrombin activity to give an estimated number for the free physiologically active thrombin.

Australian Patent Application No. 2003248589 is directed to another method for measuring thrombin potential. However, this method also includes a subtraction of the thrombin-A2M complex, detected by small substrates, from the total thrombin activity.

United States Patent Application Publication No. US 2005/0221414 is directed to a kit for measuring the thrombin generation potential in a sample of a patient's blood or plasma. In the kit described in this publication, all of the reagents such as the activator, substrate, $CaCl_2$, etc. are in a dry mixture in the container waiting for a plasma or blood to be added for assay. Again, however, this kit would measure both free thrombin and thrombin bound to A2M.

U.S. Pat. No. 6,740,496 to Hemker describes a sterically hindered substrate system that has reduced reactivity against protease-A2M complexes compared to the free proteolytic enzyme. However, the claimed substrate invention is entirely restricted to a water soluble substrate molecule with a minimum size of 10 kDa. Free thrombin determination by the soluble hindered substrate is limited in clotting plasma or blood due to a number of issues, such as: problematic detection of the reporter molecule due to quenching by protein or cells, potential absorption or aggregation of the substrate on cells or polymerizing fibrin, and inability of the substrate to react with free thrombin itself resulting from surface hindrance of extremely large molecules.

In spite of many advances in the field, there remained an unmet need for an assay that can measure free thrombin as opposed to measuring both free thrombin and thrombin bound to A2M. The present invention addresses the need for such a methodology.

SUMMARY OF THE INVENTION

The present invention provides a standardized method and reagents for the evaluation of hemorrhagic or prothrombotic tendency, as well as for assessment of anti-hemorrhagic agents and anticoagulants. In one aspect of the invention, thrombin not bound to A2M (free thrombin) can be distinguished from thrombin bound to A2M (thrombin-A2M complex).

In one aspect of the invention, a modified substrate capable of reacting with a free enzyme and not with an enzyme bound in a molecular trap is provided. The modified substrate preferably comprises a substrate attached to a macromolecule via a spacer. In a preferred embodiment, the spacer comprises 3 to 50 atoms, preferably 9 to 15 atoms, more preferably 12 atoms. In a preferred embodiment, the enzyme is a proteinase, preferably thrombin.

The macromolecule can be selected from the group consisting of: agarose beads, neutral polysaccharide ("SEPHAROSE™") beads, polystyrene beads, polyethylene, polypropylene, polyurethane, polystyrene, polyethylene oxide, polyamide, polyester, polycarbonate, polyester fiber ("DACRON™"), dextran, polytetrafluoroethylene, protein, polysaccharide, and polynucleotide. In a preferred embodiment, it is an agarose bead. In another preferred embodiment, it is polystyrene.

In another aspect, the invention provides a method of modifying a substrate. The method comprises modifying the substrate so that it cannot interact with a bound enzyme. In one embodiment, the method comprises linking the substrate to a large molecule such as an agarose bead. In another embodiment, the method comprises altering the charge, hydrophobicity or hydrophilicity of the substrate so that it is repelled by the molecule bound to the enzyme. In yet another embodiment, the substrate is modified to have affinity for a region of the enzyme-binding molecule that is distant from the exposed active site of the bound enzyme.

The invention also provides a method of detecting free versus bound enzyme in a sample. The method comprises obtaining a modified substrate as defined above, combining the substrate with the sample; and detecting a chromogenic, fluorescent or chemiluminescent signal.

In a further aspect, the invention also provides a kit for measuring enzyme activity comprising a substrate modified to react only with free enzyme.

This summary of the invention does not necessarily describe all features of the invention.

BRIEF DESCRIPTION OF THE DRAWINGS

These and other features of the invention will become more apparent from the following description in which reference is made to the appended drawings wherein.

DETAILED DESCRIPTION

Figure 1:
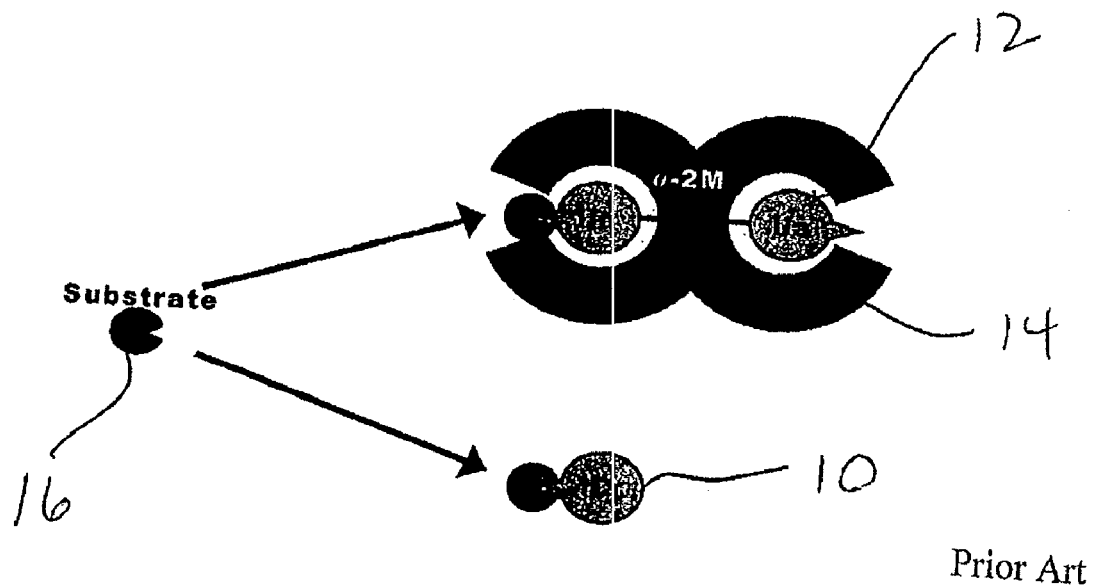
FIG. 1 is a schematic illustrating the prior art assays.

The following description is of a preferred embodiment.

The invention provides novel methodology and reagents that can be used to detect free versus bound molecules. In particular, free proteinase can be distinguished from proteinase associated with A2M. The methods and reagents can also be used to detect other proteins of diverse function in the "free" versus "bound" state.

The term "free" is used herein to refer to a moiety that is not in a complex. The term "free thrombin" refers to thrombin that is not bound to A2M, although it may be bound to other molecules.

The term "bound" is used herein to refer to a moiety that has formed a complex. The term "bound thrombin" refers to thrombin that is trapped within A2M.

The terms "substrate" and "enzyme" are used freely herein to refer to interacting components. "Substrate" refers to any moiety that can react with another moiety that can be sequestered in a molecular trap. Although the invention is described herein with specific reference to thrombin and its substrates, it is clearly apparent that the invention can be applied to many other protein-protein, receptor-ligand, enzyme-substrate reactions.

The free versus bound compound is detected using a signaling reagent that can react with the free compound, but is hindered from reacting with the bound compound. The signaling reagent can be either directly or indirectly labeled. One example of a signaling reagent is a chemiluminescent substrate that can access active sites on free enzyme, but that is unable to access the active sites of a bound enzyme.

In one aspect of the invention, a modified substrate is provided. The substrate is modified so that it can react with a free enzyme, but not with an enzyme trapped in a molecular cage. This can be achieved by coupling the substrate to a large carrier, by altering the hydrophobicity or hydrophilicity, or by changing the affinity. In a preferred embodiment, a small substrate is coupled to a macromolecule such as agarose beads, SEPHAROSE™ beads, polystyrene beads, polyethylene, polypropylene, polyurethane, polystyrene, polyethylene oxide, polyamide, polyester, polycarbonate, DACRON™, dextran, polytetrafluoroethylene, protein, polysaccharide and polynucleotide. When a substrate is attached to a large molecule, it is sterically hindered from accessing the active site of an enzyme that is sequestered in a molecular trap.

The invention also provides a method and assay for determining the quantity and/or activity of an enzyme that is actively free. The method comprises modifying a substrate as described above and determining its ability to react with an enzyme in solution. The enzyme-substrate reaction can be measured by detecting cleavage products that generate a signal.

A kit for measuring enzyme activity is also provided. The kit comprises a modified substrate that reacts only with free enzyme. The kit may also include reaction buffers and other reagents such as standardized enzyme controls or other reactants, such as tissue factor. The kit may include a surface, such as the wells of a microtitre plate or the like, that is coated with a modified substrate.

In a preferred embodiment, a thrombin-reactive substrate that is hindered from access to thrombin trapped by A2M is provided. The A2M (containing bound thrombin) either physically impedes, repels or constrains the substrate from interacting with the active site of the A2M-associated thrombin. In one embodiment, this is accomplished by construction of a substrate that is too large or the spacer too short for the thrombin-cleavable region of the substrate to protrude around the A2M portion of the thrombin-A2M complex and access (contact) the active site of the thrombin captured by the A2M. In another embodiment, groups can be bound to thrombin-cleavable substrates, which are repulsive (by charge, hydrophobicity/hydrophilicity, etc) to regions on the A2M, thus preventing the substrate's movement towards the thrombin within the thrombin-A2M complex. In a further embodiment, groups can be engineered on a thrombin-cleavable substrate, which have affinity to a region or regions of the A2M component of thrombin-A2M so that the thrombin-cleavable portion of the substrate is kept apart from the A2M-bound thrombin's active site due to association with the distant attractive locus on the A2M.

Methods and assays for measuring thrombin activity using the modified substrate are provided as well as kits for carrying out the methods.

Currently available commercial assays for determining thrombin activity utilize substrates that react with free thrombin as well as thrombin bound inside A2M. This is illustrated in FIG. 1. Free thrombin 10 and bound thrombin 12 in A2M 14 are shown to both react with the substrate 16. Thus, in order to get an estimate of the free thrombin, it is necessary to subtract a theoretical thrombin-A2M activity amount.

Figure 2:
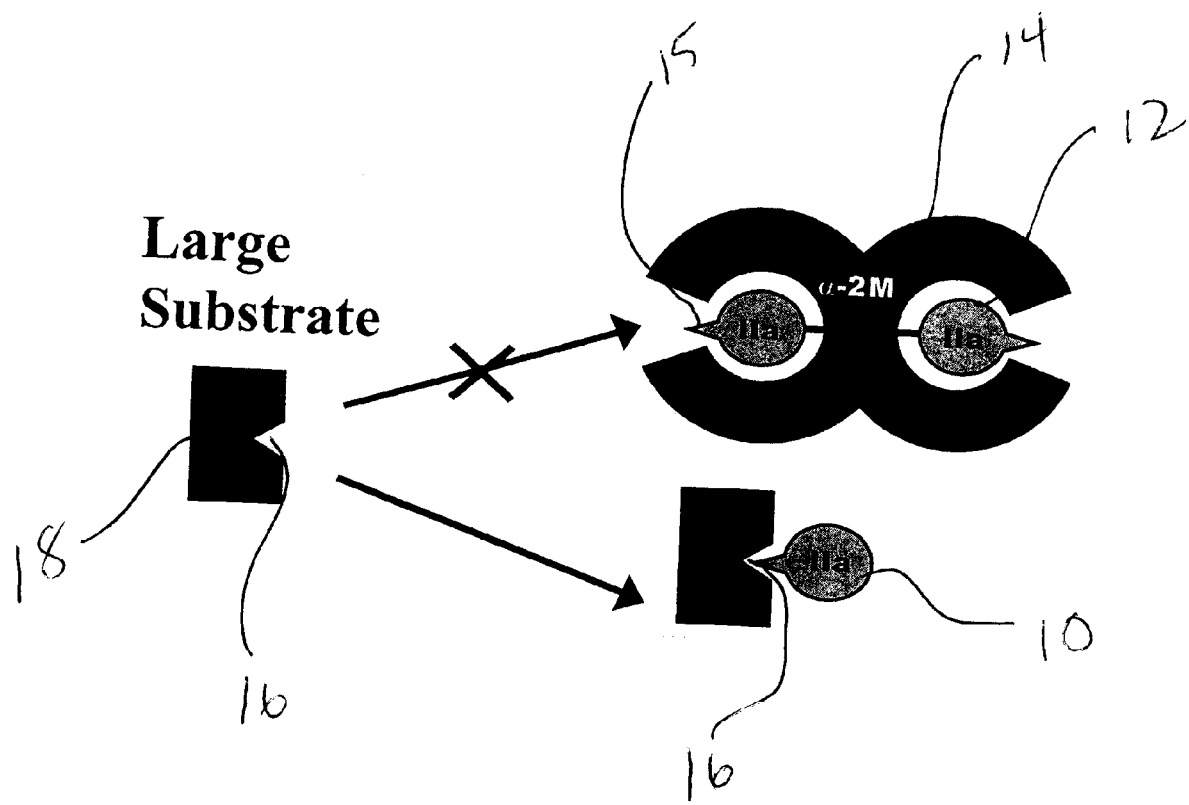
FIG. 2 illustrates how a modified substrate in accordance with an embodiment of the present invention can bind.
Figure 3:
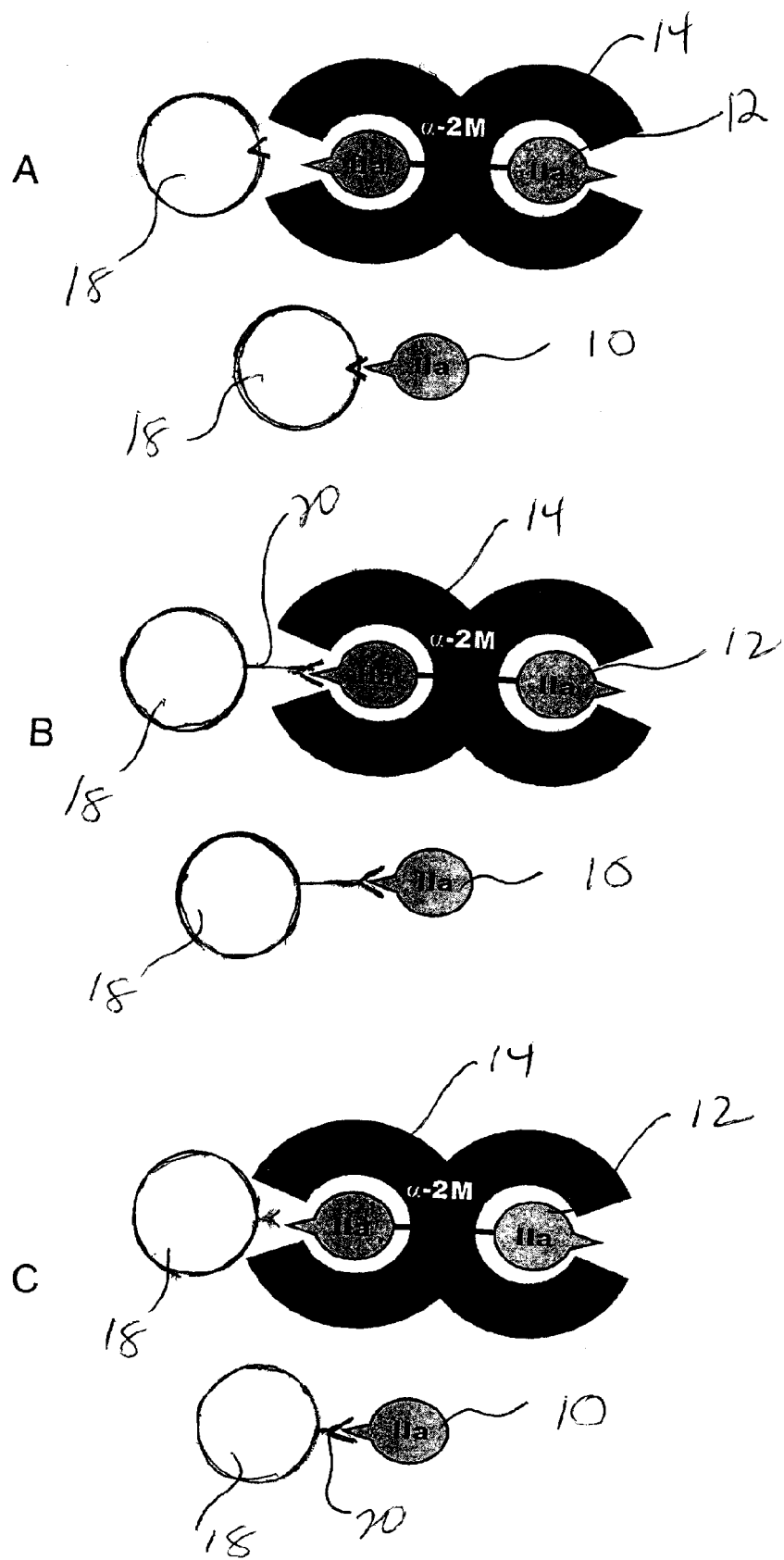
FIG. 3 illustrates how the length of the spacer can affect binding.

The problems of the prior art were overcome by linking a thrombin specific substrate onto a large matrix as illustrated schematically in FIG. 2. Thrombin is shown as free thrombin 10 and as bound thrombin 12 in A2M 14. The thrombin includes an active site 15 that can react with a substrate 16. When the substrate 16 is linked to a large matrix 18, it is sterically hindered from accessing the thrombin trapped in A2M. To achieve an optimal distinction between free 10 and bound 12 thrombin, the surface linkage of the substrate 16 to the matrix 18 should be carefully controlled. If a very short spacer 20 is used, the surface of the matrix may even hinder the free enzyme from reacting with the substrate (see FIG. 3A). If the spacer 20 is too long, the substrate may be free enough to access the bound enzyme (see FIG. 3B). For detecting free thrombin, a spacer 20 of about 5-15 atoms is preferred. This spacer is long enough to allow the substrate to react with the free enzyme, but not long enough to allow it to access the bound enzyme (see FIG. 3C). A spacer of 8-14, preferably 12, atoms is particularly useful for coupling a substrate to an agarose bead.

Figure 4:
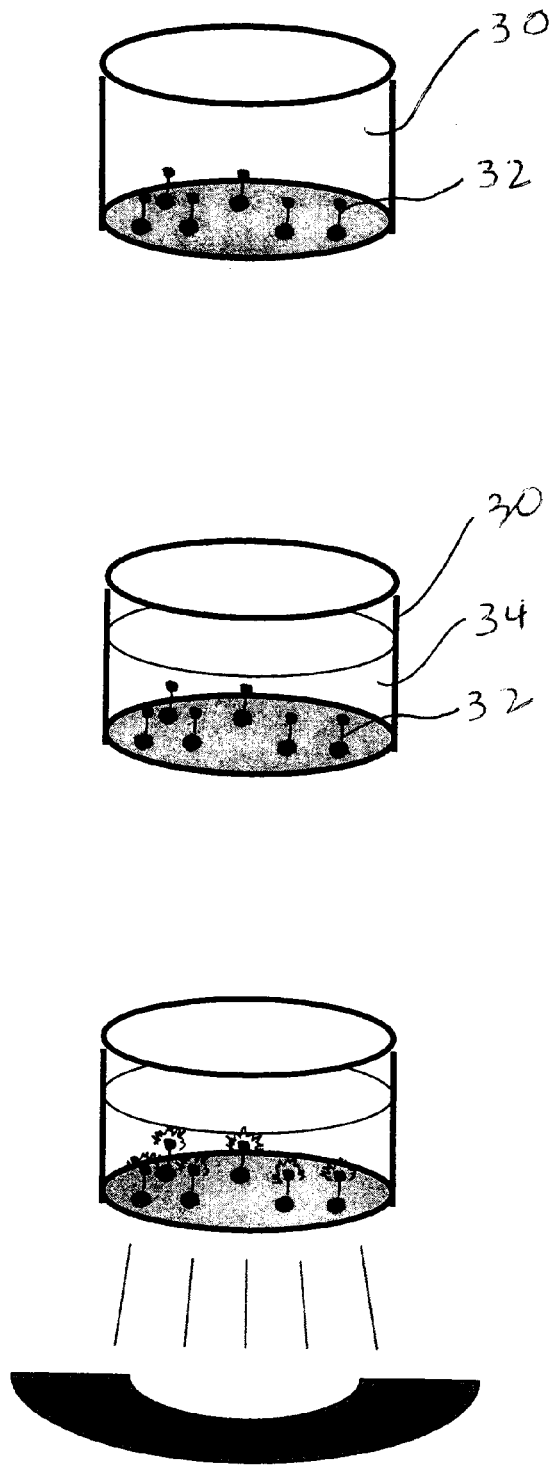
FIG. 4 illustrates an assay of one aspect of the invention.

FIG. 4 illustrates how the modified substrate of the invention can be used in an assay. A well 30 of a microtitre plate is coated with a matrix-modified chemiluminescent thrombin substrate 32. Plasma or blood 34 is added to the well. Thrombin from activated blood or plasma reacts with the substrate and a signal is generated and detected by a luminometer. While it is preferable to use a chemiluminescent detector, it is clearly apparent that other detection means known to those in the art can be used to detect binding of the modified substrate to the free enzyme. It is apparent that modified substrates can also be coated onto other surfaces such as test tubes and tubing. Also, it should be understood that coating of modified substrates can be through either covalent or non-covalent linkage to a surface.

Figure 5:
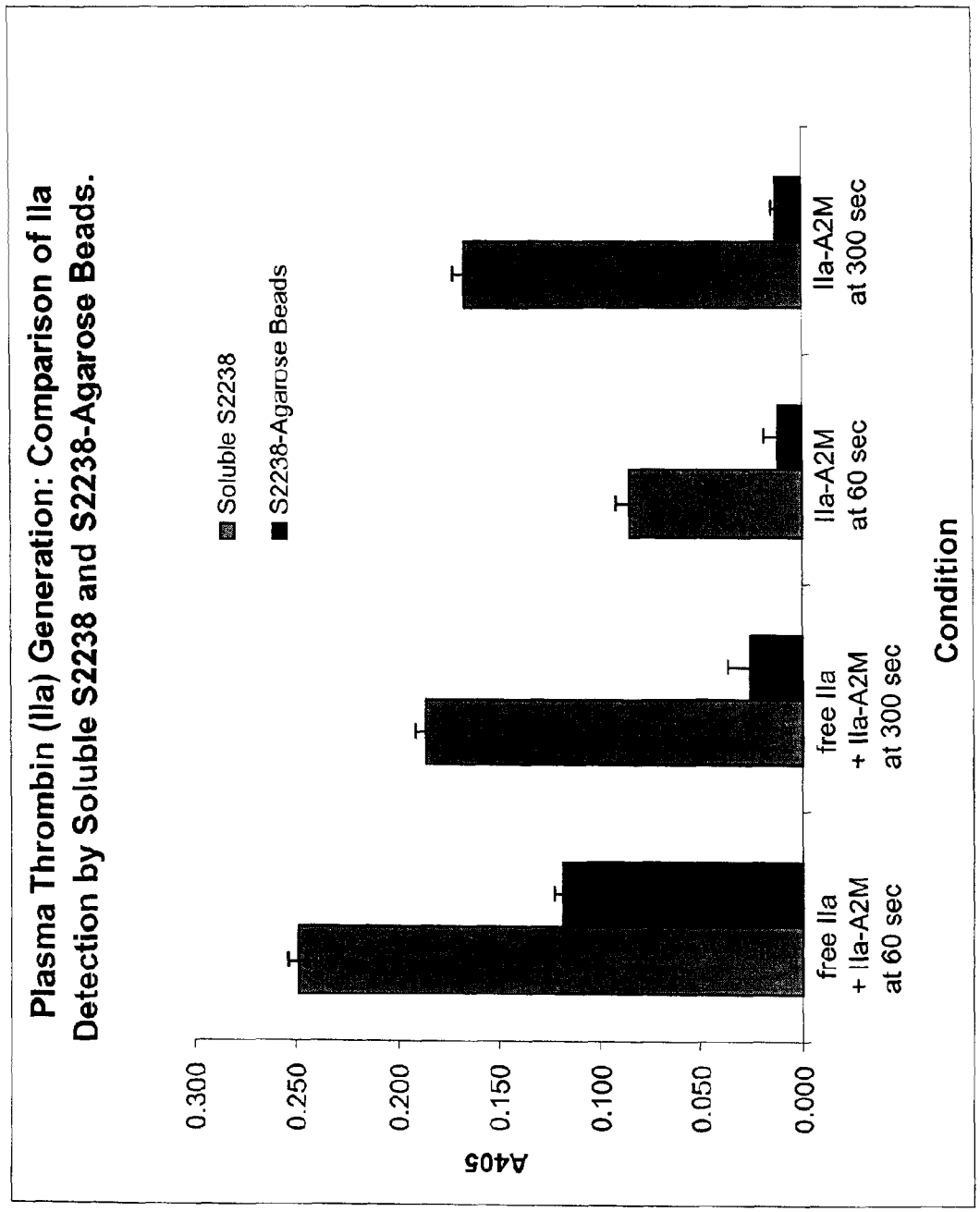
FIG. 5 illustrates results from a thrombin generation assay.

FIG. 5 illustrates how the present invention can be used to measure thrombin generation. The results indicate that the modified substrate of the invention can distinguish between free thrombin and thrombin-A2M complexes.

The invention provides a novel method in which thrombin not bound to A2M is measured directly, while in the presence of thrombin-A2M complexes, without detecting thrombin-A2M. The invention provides a simple method for measuring free thrombin without having to do any further manipulation or mathematical derivation to determine the level of free thrombin that is generated. The modified substrates of the invention restrict reaction with thrombin bound to A2M. However, thrombin localized on some surfaces may react with substrates that are sterically hindered from approach to thrombin held within an A2M complex. This may be accomplished by a special feature of the invention, whereby a spacer of optimal length is used to link the sterically hindering macromolecule to the reactive substrate. A substrate that can react with thrombin on surfaces (such as fibrin or platelets), but not thrombin bound to A2M, may mimic the reactivity of fibrinogen (or other biological macromolecules/systems) with thrombin generated in vivo.

Another advantage of the substrates of the invention is that it is possible to separate the substrates from the reacting thrombin when the thrombin-reactive substrate is bound to molecules that are large enough to be precipitated, manually removed, ionically extracted or hydrophobically absorbed.

The present method allows one to determine thrombin not bound to A2M in the presence of thrombin-A2M using a single assay (one step). When continuous thrombin generation analysis is carried out in clotting plasma or blood, previous methods relied on fluorogenic thrombin substrates reacting in the plasma/blood. However, the fluorescent products in these experiments suffer from excitation interference and emission quenching from molecules and cells in the plasma or blood. The present invention overcomes this interference with detection of fluorescence in the fluid phase by attachment of thrombin substrate to the container wall so that any signal from the thrombin-cleavage product can be measured by direct observation of the product light traveling through the container wall away from (instead of through) the plasma/blood milieu.

This invention may be used to directly measure thrombin generation in plasma or blood over time in vitro without having to extract contaminating measurement of thrombin-A2M. The direct thrombin activity detecting substrate(s) allow for a simple streamlined assay for thrombin potential in plasma or blood and provide a standard measure of hemorrhagic or prothrombotic tendency, as well as anti-hemorrhagic agent or anticoagulant assessment for routine clinical practice.

Substrates that are sterically hindered from reacting with thrombin-A2M via covalent/non-covalent binding to the inner surface of a transparent container, make it possible to detect the thrombin substrate cleavage products (i.e. chromogenic, fluorogenic or chemiluminescent products) without any interference from other molecules (such as plasma/blood proteins) in the reaction mixture.

Furthermore, when groups with high affinity for thrombin are immobilized to a surface that sterically prevents binding to thrombin associated with A2M, this material can be used to isolate non-A2M bound thrombin from the medium. This is useful for immunological, fine structural and other investigations.

In addition, when a modified substrate binds thrombin in a fluid phase, and inhibits A2M binding either by size, charge or affinity to separate regions of A2M, subsequent thrombin interactions which depend on other mechanisms of binding can be studied, including localization of thrombin binding to either platelet or vascular endothelial surfaces under a variety of conditions.

Although preferred embodiments of the invention have been described in detail, it is apparent that a substrate modified to react with free, but not bound enzyme would be useful in a variety of assays and applications.

The above disclosure generally describes the present invention. It is believed that one of ordinary skill in the art can, using the preceding description, make and use the compositions and practice the methods of the present invention. A more complete understanding can be obtained by reference to the following specific examples. These examples are described solely to illustrate preferred embodiments of the present invention and are not intended to limit the scope of the invention. Changes in form and substitution of equivalents are contemplated as circumstances may suggest or render expedient. Other generic configurations will be apparent to one skilled in the art. All journal articles and other documents such as patents or patent applications referred to herein are hereby incorporated by reference.

EXAMPLES

Although specific terms have been used in these examples, such terms are intended in a descriptive sense and not for purposes of limitation. Methods of biochemistry and chemistry referred to but not explicitly described in the disclosure and these examples are reported in the scientific literature and are well known to those skilled in the art.

Example 1

Preparation of a S2238—Agarose Modified Substrate

A thrombin substrate S2238 (Diapharma, West Chester, Ohio, USA) was reacted with Epoxy-Agarose (Sigma, Mississauga, Ontario, Canada; Agarose bead matrix with a 12 atom spacer ending in a reactive epoxide functional group) to produce S2238-Agarose (S2238 linked to Agarose through a 12 atom spacer group) according to the manufacturer's instructions. One bottle containing 25 mg of S2238+other solids (Lot # N0548870) from DiaPharma was dissolved in 2 mL of $H_2O$ and 1 mL of the resultant solution taken for conjugation with 1 g of dried epoxy-activated Agarose (beads swollen and washed prior to mixing with S2238). Phosphate pH 9.0 was used for the conjugation reaction (reaction solution mixed by inversion at 23° C. for 16 hours). Excess epoxy groups were blocked by reaction with 1 M Tris.HCl pH 9.0 for 4 hours. Beads from the final reaction mixture were washed with alternating 0.1 M Na acetate titrated to pH 4.0 with conc. HCl (acetate buffer) and 0.1 M $H_3BO_3$ 0.5 M NaCl pH 8.0. The S2238-Agarose beads were then stored as a 50% suspension in acetate buffer at 4° C.

Example 2

Comparison of Reactivity of Substrate and Modified Substrate

The reactivity of thrombin substrate S2238 and S2238-Agarose with free thrombin and thrombin A2M complex was determined.

A solution of 0.05 M HEPES 0.15 M NaCl pH 7.5 (HBS) was prepared. Thrombin-A2M was prepared by reaction of 40 μL of 5 mg A2M (Sigma)/mL+40 μL of 0.2 mg thrombin (Enzyme Research Laboratories, South Bend, Ind., USA)/mL HBS for 40 to 60 minutes at 23° C. (solution #1). Solutions of 40 μL of 5 mg A2M/mL+40 μL HBS (solution #2) and 40 μL of 0.2 mg thrombin/mL+40 μL HBS (solution #3) were prepared.

The following reactions with S2238 were carried out in 96-well plate wells.

1. 5 μL of solution #1 were added to 10 uL of 0.5 mg antithrombin (purified antithrombin III protein, Affinity Biologicals, Ancaster, Ontario, Canada)/mL HBS+1 μL of 100 U heparin (Leo Laboratories, Ajax, Ontario, Canada)/mL HBS+74 μL HBS. After 10 minutes, 10 μL of 3.192 mg S2238/mL $H_2O$ was added with mixing, absorbance readings at 405 nm measured every 10 seconds for 100 seconds and the change in absorbance over that time recorded (ΔA).
2. 5 μL of solution #2 were added to 10 uL of 0.5 mg antithrombin/mL HBS+1 μL of 100 U heparin/mL HBS+74 μL HBS. After 10 minutes, 10 μL of 3.192 mg S2238/mL $H_2O$ was added with mixing, absorbance readings at 405 nm measured every 10 seconds for 100 seconds and the change in absorbance over that time recorded (ΔA).
3. 5 μL of solution #3 were added to 10 uL of 0.5 mg antithrombin/mL HBS+1 μL of 100 U heparin/mL HBS+74 μL HBS. After 10 minutes, 10 μL of 3.192 mg S2238/mL $H_2O$ was added with mixing, absorbance readings at 405 nm measured every 10 seconds for 100 seconds and the change in absorbance over that time recorded (ΔA).
4. 5 μL of solution #1 were added to 85 uL of HBS. After 10 minutes, 10 μL of 3.192 mg S2238/mL $H_2O$ was added with mixing, absorbance readings at 405 nm measured every 10 seconds for 100 seconds and the change in absorbance over that time recorded (ΔA).
5. 5 μL of solution #2 were added to 85 uL of HBS. After 10 minutes, 10 μL of 3.192 mg S2238/mL $H_2O$ was added with mixing, absorbance readings at 405 nm measured every 10 seconds for 100 seconds and the change in absorbance over that time recorded (ΔA).
6. 5 μL of solution #3 were added to 85 uL of HBS. After 10 minutes, 10 μL of 3.192 mg S2238/mL $H_2O$ was added with mixing, absorbance readings at 405 nm measured every 10 seconds for 100 seconds and the change in absorbance over that time recorded (ΔA).

S2238-Agarose beads (stored with an equal volume of acetate buffer) were well mixed and 0.25 mL aliquots of the resultant homogeneous suspension were taken into eppendorf tubes. After centrifuging and carefully removing the supernatant, the beads in each tube were mixed with 0.5 mL of 0.02 M Tris.HCl 0.15 M NaCl 0.6% polyethylene glycol 8000 pH 7.4 (TSP), centrifuged and the supernatant removed. The beads were mixed with TSP again, centrifuged and the supernatant carefully removed in preparation for reaction with various materials. The following reactions with the washed S2238-Agarose beads were carried out.

1. 30 μL of solution #1 was mixed with 570 μL of HBS and 0.25 mL of the resultant solution mixed with washed beads in the eppendorf tube. After either 3 or 10 minutes at 23° C., the tube was centrifuged for 1 minute and the supernatant quickly (but carefully) placed in an eppendorf tube. One hundred μL of the reaction supernatant was placed in a 96-well plate well and the absorbance at 405 nm measured (end point reading).
2. 30 μL of solution #3 was mixed with 570 μL of HBS and 0.25 mL of the resultant solution mixed with washed beads in the eppendorf tube. After either 3 or 10 minutes at 23° C., the tube was centrifuged for 1 minute and the supernatant quickly (but carefully) placed in an eppendorf tube. One hundred μL of the reaction supernatant was placed in a 96-well plate well and the absorbance at 405 nm measured (end point reading).
3. 30 μL of solution #3 was mixed with 60 μL of 0.5 mg antithrombin/mL HBS+6 μL of 1000 U heparin/mL HBS+504 μL of HBS and 0.25 mL of the resultant solution mixed with washed beads in the eppendorf tube. After either 3 or 10 minutes at 23° C., the tube was centrifuged for 1 minute and the supernatant quickly (but carefully) placed in an eppendorf tube. One hundred μL of the reaction supernatant was placed in a 96-well plate well and the absorbance at 405 nm measured (end point reading).
4. 0.25 mL of HBS was mixed with washed beads in the eppendorf tube.
   After either 3 or 10 minutes at 23° C., the tube was centrifuged for 1 minute and the supernatant quickly (but carefully) placed in an eppendorf tube. One hundred μL of the reaction supernatant was placed in a 96-well plate well and the absorbance at 405 nm measured (end point reading).

The results of the reactions are shown in Tables 1 and 2 below.

TABLE 1

Reactions with soluble S2238.

| Reaction # | Reactants added to S2238 | ΔA |
|---|---|---|
| 1 | thrombin-A2M + antithrombin + heparin | 0.8 |
| 2 | A2M + antithrombin + heparin | 0 |
| 3 | thrombin + antithrombin + heparin | 0 |
| 4 | Thrombin-A2M | 0.8 |
| 5 | A2M | 0 |
| 6 | Thrombin | 0.95 |

TABLE 2

Reactions with S2238-Agarose.

| Reaction # | Reactants added to Beads | Absorbance after 3 minutes of reaction | Absorbance after 10 minutes of reaction |
|---|---|---|---|
| 1 | thrombin-A2M | 0.056 | 0.067 |
| 1 | thrombin-A2M | 0.058 | 0.068 |
| 2 | Thrombin | 0.464 | 0.741 |
| 2 | Thrombin | 0.472 | 0.735 |
| 3 | thrombin + antithrombin + heparin | 0.047 | 0.049 |
| 3 | thrombin + antithrombin + heparin | 0.047 | 0.046 |
| 4 | Buffer | 0.046 | 0.044 |
| 4 | Buffer | 0.043 | 0.045 |

The data presented in Tables 1 and 2 above indicate that while S2238 reacts readily with either free thrombin or thrombin-A2M, the S2238-Agarose beads react significantly with free thrombin but not with thrombin-A2M.

Example 3

Further Comparison of Reactivities

Thrombin and thrombin-A2M were added to samples of S2238 and S2238-Agarose. The change in absorbance was detected and the results are shown in Table 3 below.

TABLE 3

| REACTANTS | Thrombin Activity (Δ absorbance/minute) | |
|---|---|---|
| | S2238 | S2238-Agarose |
| Thrombin | 0.57 | 0.141 |
| thrombin-A2M | 0.48 | 0.004 |

The results indicate that the modified substrate S2238-Agarose reacted strongly with the free thrombin, but not with the bound thrombin.

Example 4

Reaction of Thrombin with S2238 Immobilized by Reaction of S2238 with CNBr-activated SEPPHAROSE™

To confirm the requirement of a minimum number of atoms in the spacer between substrate and hindering macromolecular surface, reaction of thrombin was tested with S2238 linked to SEPHAROSE™ beads by a small CNBr activation group.

Preparation of S2238-SEPHAROSE™

One bottle of unsuspended (dry) powder containing 25 mg of S2238 (Chromogenix Lot NO526873) was suspended in 2 mL of $H_2O$. One mL of the suspension was removed and placed in a 50 mL capped plastic centrifuge tube with 0.75 mL of 1.75 mL of 0.2 M $NaHCO_3$ 1 M NaCl pH 8.0. One g of CNBr-activated SEPHAROSE™ (Amersham Biosciences Lot No. 299594) was suspended (swollen) in 10 mL of 0.001 M HCl and then washed with 200 mL of 0.001 M HCl on a sintered glass filter. The washed CNBr-activated SEPHAROSE™ was placed in the tube with the S2238 solution and incubated on a rocker plate for 2 hours at 23° C., followed by incubation on the rocker plate for 18 hours at 4° C. Following reaction, the beads in the reaction mixture were washed on a sintered glass filter with 100 mL of 0.1 M $NaHCO_3$ 0.5 M NaCl pH 8.0. Washed beads were added to a 50 mL capped plastic centrifuge tube containing 15 mL of 0.1 M Tris.HCl pH 8.0 and incubated on a rocker plate for 2 hours at 23° C. Beads were then washed on a sintered glass filter with 10 mL of 0.1 M Tris.HCl 0.5 M NaCl pH 8.0, followed by 20 mL of 0.1 M sodium acetate 0.5 M NaCl pH 4.0. This latter washing with Tris.HCl/NaCl and sodium acetate/NaCl was repeated 5 more times. Finally the beads were stored in a capped plastic tube with an equal volume (to that of the packed beads) of 0.1 M sodium acetate 0.5 M NaCl pH 4.0 at 4° C. This stock of stored beads was designated S2238-SEPHAROSE. Mixture of a small subsample of S2238-SEPHAROSE™ bead suspension with an equal volume of 4 M NaOH gave a strong yellow colour in the fluid phase (absorbing at 405 nm), confirming attachment of intact S2238 substrate to the SEPHAROSE™ beads.

Reaction with Thrombin 0.5 mL of resuspended S2238-SEPHAROSE™ beads was placed in each of 2 microfuge tubes (1.5 mL capacity), followed by centrifugation at 12000 g for 1 minute and removal of the resultant supernatant. Beads in each tube were resuspended in 0.5 mL of 0.02 M Tris-HCl 0.15 M NaCl 0.6% polyethylene glycol 8000 pH 7.4 (TSP), centrifuged for 1 minute and the resultant supernatant discarded. A solution of 100 nM human alpha thrombin (Enzyme Research Laboratories) in TSP was prepared. 0.5 mL of thrombin was added to one tube of packed S2238-SEPHAROSE™ beads (tube 1) and 0.5 mL of TSP was added to the other tube of S2238-SEPHAROSE™ beads (tube 2). In a separate empty tube, 0.05 mL of free (not conjugated to beads) S2238 stock solution (12.5 mg of S2238/mL of H2O)+0.15 mL of TSP+0.5 mL of 100 nM thrombin were added (tube 3). Finally, in a separate empty tube, 0.05 mL of free S2238 stock solution+0.65 mL of TSP were added (tube 4). All of the tubes were capped and tubes+contents were gently shaken by inversion manually for 10 min at 23° C. Following inversion mixing, tubes were centrifuged at 12000 g for 1 min and 0.2 mL of supernatant fluid from each tube quickly removed to separate wells of a 96-well microtitre plate and the absorbance at 405 nm measured.

Results:

Absorbance readings from the different incubation mixtures are given below.

| Tube Number | Incubation mixture | Absorbance at 405 nm of supernatant after 10 minutes incubation and 1 minute centrifugation |
|---|---|---|
| 1 | S2238-SEPHAROSE ™ beads + thrombin + TSP buffer | 0.050 |
| 2 | S2238-SEPHAROSE ™ + TSP buffer | 0.052 |
| 3 | Free unbound S2238 + thrombin + TSP buffer | 1.143 |
| 4 | Free unbound S2238 + TSP buffer | 0.043 |

These data clearly show that S2238 attached to macroscopic beads through a CNBr activation group (ie. a —NH—(C=NH)—O— linkage) does not allow reaction with thrombin itself. Thus, linkage of the substrate and macromolecular surface by a spacer that contains a relatively small number of atoms does not allow enough relief from steric hindrance for even the free enzyme to react with the substrate.

Example 5

Plasma Thrombin Generation Determined by Either Free S-2238 or S2238-Agarose

Plasma is taken and the fibrinogen removed by reaction with ancrod enzyme to form a fibrin clot that is wound out to give the resultant defibrinated plasma. At time zero, tissue factor (Thromborel S)+$CaCl_2$ are added to start thrombin generation in the pre-warmed defibrinated plasma. At certain time points, subsamples from the reaction mixture are taken into $Na_2EDTA$ to stop further thrombin generation by chelating the $Ca^{2+}$. Thrombin activity in the time sample (containing both free thrombin and thrombin bound to alpha-2-macroglobulin (A2M)) was then detected by mixing with either free S2238 substrate in buffer or sterically hindered S2238 substrate (S2238-Agarose beads) suspended in buffer. In order to determine the ability of free S2238 or S2238-Agarose to detect thrombin-A2M, a similar experiment to the above method was carried out, except that all free thrombin was inhibited first by mixing with antithrombin+heparin prior to incubation with substrate. During the time course of plasma thrombin generation, prothrombin is initially converted to thrombin and then the free thrombin is progressively inhibited by either plasma antithrombin (no chromogenic activity against free S2338) or A2M (thrombin bound to A2M retains activity against small chromogenic S2238 substrate). Thus, early time point samples (ie. 60 seconds) would contain more free thrombin than thrombin-A2M, while later time point samples (ie. 300 seconds) would contain much more thrombin-A2M than free thrombin.

Measurement of Total Thrombin (Free Thrombin+thrombin-A2M) Generation in Plasma 12 mm (ID)×75 mm (L) polycarbonate plastic test tubes were used for plasma thrombin generation.

1. Defibrination of Plasma:
    a. 800 μL of Plasma was incubated with 10 μL of 30 U/mL Ancrod stock at 37° C. for 10 minutes.
    b. After incubation, fibrin clot that formed was wound out on a plastic rod, leaving supernatant defibrinated plasma.
    c. Test tube was placed on ice for 10 minutes.
    d. After 10-minute incubation, any further clots were wound out.
    e. Defibrinated plasma was stored on ice.
2. The activator solution (12.5 μL Thromborel S + 4.0 μL 1M $CaCl_2$ + 183.5 μL HBS) was warmed at 37° C. in a tube. In a separate tube, 150 μL of defibrinated plasma was warmed at 37° C.
3. At t = 0, 150 μL of activator solution was mixed with 150 μL of defibrinated plasma, at 37° C.
4. At both t = 60 and t = 300 seconds, 25 μL of the reaction mixture were removed and immediately added to 475 μL of 0.005M $Na_2EDTA$ on ice.
5. Once all time points were neutralized with EDTA, 50 μL of each EDTA/time sample was mixed with 135 μL of Beads suspended in HBS (approximately 75 μL of packed beads, with a final S2238 concentration in the bead suspension of 0.35 mM) in a microfuge tube at 37° C. The time sample aliquot + bead suspension were mixed by inversion throughout the ensuing incubation.
6. In separate tubes, 50 μL of the EDTA/time sample was added to 110 μL of 0.00016M S-2238 in HBS at 37° C.
7. After 10 minutes of incubation with either free S2238 substrate or S2238-Agarose beads, 40 μL of 50% acetic acid was added to each tube in order to stop substrate hydrolysis.
8. The microfuge tubes containing acetic acid neutralized bead suspensions were micro-centrifuged for 1 minute.
9. Aliquots of 200 μL of supernatant from each sample were placed in 96-well plate wells and the absorbance at 405 nm measured.

Measurement of Thrombin-A2M Generated in Plasma

The experiment described above was repeated, except that at step 4, 25 μL of time sample was added to 5 μL of 50 U antithrombin/mL PBS (7.2 mg antithrombin/mL)+2 μL of 100 U heparin/mL 0.15 M NaCl on ice. After 1 minute, 468 μL of 0.005 M $Na_2EDTA$ was added and the procedure continued as before. Absorbance detected at 405 nm was essentially due to substrate reaction with thrombin-A2M alone (free thrombin having been neutralized by antithrombin+heparin).

The absorbance due to substrate cleavage by free thrombin in the time samples could be determined by subtracting the absorbance due to thrombin-A2M from the absorbance in the initial experiments (in which time samples were not neutralized with antithrombin+heparin and contained both free thrombin+thrombin-A2M).

The data shown in FIG. 5 illustrate that in plasma samples containing generated free thrombin+thrombin complexed to A2M, significant activity was detected by both soluble (free) S2238 and S2238-Agarose beads at 60 seconds after plasma activation. At 300 seconds after plasma activation, significant thrombin substrate activity was measured with soluble S2238, but S2238-Agarose beads gave relatively reduced amounts of thrombin activity (absorbance at 405 nm). However, in plasma samples where generated thrombin-A2M complexes, but not free thrombin, remained (free thrombin neutralized by antithrombin+heparin), significant thrombin activity was detected by soluble S2238 (especially at the 300 sec time point) while only baseline background absorbance was measured by sterically hindered S2238-Agarose beads. Comparison of plasma samples containing generated free thrombin+thrombin-A2M with those containing only thrombin-A2M shows that, 300 sec after addition of calcium+tissue factor, the vast majority of soluble S2238 activity is due to thrombin-A2M. In the case of S2238-Agarose beads, only free thrombin is detected at either 60 sec or 300 sec time points.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

1. Schenone M, Furie B C, Furie B. The blood coagulation cascade. Curr Opin Hematol. 11(4):272-277, 2004.
2. Walsh P N. Platelet coagulation-protein interactions. Semin Thromb Hemost. 30(4):461-471, 2004.
3. Suo Z, Citron B A, Festoff B W. Thrombin: a potential proinflammatory mediator in neurotrauma and neurodegenerative disorders. Curr Drug Targets Inflamm Allergy. 3(1):105-114, 2004.
4. Standeven K F, Ariens R A, Grant P J. The molecular physiology and pathology of fibrin structure/function. Blood Rev. 19(5):275-288, 2005.
5. Weisel J W. Fibrinogen and fibrin. Adv Protein Chem. 70:247-299, 2005.
6. Andrew M, Paes B, Milner R, Johnston M, Mitchell L, Tollefsen D M, Powers P. Development of the human coagulation system in the full-term infant. Blood. 70(1):165-172, 1987.
7. Andrew M, Paes B, Milner R, Johnston M, Mitchell L, Tollefsen D M, Castle V, Powers P. Development of the human coagulation system in the healthy premature infant. Blood. 72(5):1651-1657, 1988.
8. Andrew M, Vegh P, Johnston M, Bowker J, Ofosu F, Mitchell L. Maturation of the hemostatic system during childhood. Blood. 80(8):1998-2005, 1992.
9. Sottrup-Jensen L. Alpha-macroglobulins: structure, shape, and mechanism of proteinase complex formation. J Biol Chem. 264(20):11539-11542, 1989.
10. Niemuller C A, Randall K J, Webb D J, Gonias S L, Lamarre J. Alpha-2-macroglobulin conformation determines binding affinity for activin A and plasma clearance of activin A/alpha-2-macroglobulin complex. Endocrinology. 136(12):5343-5349, 1995.
11. Steiner J P, Bhattacharya P, Strickland D K. Thrombin-induced conformational changes of human alpha 2-macroglobulin: evidence for two functional domains. Biochemistry. 24(12):2993-2300, 1985.
12. Feinman R D, Yuan A I, Windwer S R, Wang D. Kinetics of the reaction of thrombin and alpha 2-macroglobulin. Biochem J. 231(2):417-423, 1985.
13. Massicotte P, Leaker M, Marzinotto V, Adams M, Freedom R, Williams W, Vegh P, Berry L, Shah B., Andrew M. Enhanced thrombin regulation during warfarin therapy in children compared to adults. Thromb Haemost. 80(4):570-574, 1998.
14. Andrew M, Berry L, O'Brodovich H. Thrombin inhibition by fetal distal lung epithelium is different in fetal and adult plasma. Am J Respir Cell Mol Biol. 11(1):35-41, 1994.
15. Cvirn G, Gallistl S, Koestenberger M, Kutschera J, Leschnik B, Muntean W. Alpha 2-macroglobulin enhances prothrombin activation and thrombin potential by inhibiting the anticoagulant protein C/protein S system in cord and adult plasma. Thromb Res. 105(5):433-439, 2002.
16. Hemker H C, Wielders S, Kessels H, Beguin S. Continuous registration of thrombin generation in plasma, its use for the determination of the thrombin potential. Thromb Haemost. 70(4):617-624, 1993.
17. Kessels H, Willems G, Hemker H C. Analysis of thrombin generation in plasma. Comput Biol Med. 24(4):277-288, 1994.
18. Hemker H C, Giesen P L, Ramjee M, Wagenvoord R, Beguin S. The thrombogram: monitoring thrombin generation in platelet-rich plasma. Thromb Haemost. 83(4):589-591, 2000.
19. Streif W, Paes B, Berry L, Andreasen R B, Chan A K. Influence of exogenous factor VIIa on thrombin generation in cord plasma of full-term and pre-term newborns. Blood Coagul Fibrinolysis. 11(4):349-357, 2000.
20. Meddahi S, Bara L, Fessi H, Samama M M. Determination of prothombinase activation after adding human purified prothrombin to human clot: comparison of hirudin, an activated factor II inhibitor, with DX9065a, an activated factor X inhibitor, on clot-associated thrombin and on prothrombin activation. Blood Coagul Fibrinolysis. 16(2):125-133, 2005.

What is claimed is:

1. A modified peptide substrate that is modified by attaching a macromolecule via a spacer that comprises 9-15 atoms, wherein the modified peptide substrate is cleavable by a free proteinase but not by a proteinase bound in a molecular trap, and wherein the peptide substrate is S2238, and the proteinase is thrombin.

2. The modified peptide substrate of claim 1, wherein the macromolecule is selected from the group consisting of agarose beads, polystyrene beads, polyethylene, polypropylene, polyurethane, polystyrene, polyethylene oxide, polyamide, polyester, polycarbonate, dextran, polytetrafluoroethylene, protein, polysaccharide, and polynucleotide.

* * * * *